US009211695B2

(12) United States Patent
Paulson

(10) Patent No.: US 9,211,695 B2
(45) Date of Patent: Dec. 15, 2015

(54) LOW-COST MEASUREMENT SYSTEM FOR PHOTOPOLYMER FILM POLYMERIZATION MONITORING

(75) Inventor: Christopher Paulson, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 203 days.

(21) Appl. No.: 13/471,749

(22) Filed: May 15, 2012

(65) Prior Publication Data
US 2013/0306872 A1 Nov. 21, 2013

(51) Int. Cl.
| G01N 21/55 | (2014.01) |
| B41F 23/04 | (2006.01) |
| C09D 11/101 | (2014.01) |
| G01N 33/32 | (2006.01) |
| G01N 21/84 | (2006.01) |
| G01N 21/3577 | (2014.01) |
| G01N 21/3563 | (2014.01) |
| B05D 3/02 | (2006.01) |
| B05D 3/06 | (2006.01) |

(52) U.S. Cl.
CPC ......... *B41F 23/0409* (2013.01); *B41F 23/0413* (2013.01); *B41F 23/0453* (2013.01); *B41F 23/0456* (2013.01); *C09D 11/101* (2013.01); *G01N 21/3577* (2013.01); *G01N 21/55* (2013.01); *G01N 21/8422* (2013.01); *G01N 33/32* (2013.01); *B05D 3/0263* (2013.01); *B05D 3/067* (2013.01); *G01N 21/3563* (2013.01); *G01N 2021/8411* (2013.01); *G01N 2021/8427* (2013.01)

(58) Field of Classification Search
CPC .............. G01N 2021/8427; G01N 2021/8438; G01N 2021/8472
See application file for complete search history.

(56) References Cited

U.S. PATENT DOCUMENTS

| 4,015,127 A * | 3/1977 | Sharkins .................... 250/341.3 |
| 4,092,443 A * | 5/1978 | Green ........................... 427/519 |
| 5,391,685 A * | 2/1995 | Hitomi et al. .................... 528/75 |
| 7,145,147 B1 * | 12/2006 | Shelley et al. ........... 250/339.11 |
| 8,189,189 B1 * | 5/2012 | Herendeen et al. ........... 356/300 |
| 2012/0180561 A1 * | 7/2012 | Hirning et al. .............. 73/150 R |

FOREIGN PATENT DOCUMENTS

JP  2008157634 A  *  7/2008

OTHER PUBLICATIONS

Machine translation of JP 2008-157634 A.*

* cited by examiner

*Primary Examiner* — Constantine Hannaher
(74) *Attorney, Agent, or Firm* — Marger Johnson

(57) ABSTRACT

A monitoring device includes a light source, an optical filter, and an optical detector. The monitoring device may monitor curing processes, such as ultraviolet (UV) curing processes to determine the progression of the level of cure of a light-activated material to a substrate. The light source emits light toward a light-activated material, such as a film, and/or a substrate. The optical filter is positioned so that a wavelength of the light is transmitted through the optical filter after the light is reflected off of the substrate and/or the film. The optical detector is positioned to detect the light that is transmitted through the optical filter.

22 Claims, 2 Drawing Sheets

LOW-COST MEASUREMENT SYSTEM FOR PHOTOPOLYMER FILM POLYMERIZATION MONITORING

BACKGROUND

Light curing processes have become very popular and useful in a wide variety of applications including printing, coating, adhesives, and the like. Many types of curing processes exist such as arc lamp and ultraviolet light-emitting diode (LED) curing processes. These curing processes alter the chemical and physical properties and structures of a light-activated material so that the material becomes "cured" to a substrate through the curing process.

One critical aspect of the light-curing process is to determine when a light-activated material has completed or is nearing completion of the curing process. An indication of completion of the curing process is to measure the extent of polymerization of the light-activated material. This determination is typically performed by Fourier transform infrared (FTIR) spectroscopy methods, which require equipment that is expensive to manufacture and maintain. Alternatively, rub or tape tests are used to determine whether the curing process is complete, which are rudimentary and subjective tests and thus require significant amounts of training the testers to perform the tests correctly and reach an accurate test result. Both the FTIR spectroscopy and the rub and tape tests are performed after the curing process has been estimated to be completed and are not done in real-time. Because the curing process is stopped to perform these tests, the overall process takes more time to complete, which reduces efficiency. Further, the rub and tape tests are very rudimentary tests that can be subjective and inefficient, which leaves room for error and a reduction in productivity.

Accordingly, there remains a need for an improved monitoring device that can detect the level of cure of light-activated materials in an accurate and cost-effective manner.

SUMMARY

A measurement device has a light source, an optical filter, and an optical detector. The light source emits light and the optical filter is positioned so that a wavelength of the light is transmitted through the optical filter after the light is reflected off of at least one of a substrate and a film cured to the substrate. The optical detector is positioned to detect the light that is transmitted through the optical filter.

A method includes emitting light from a light source toward a film cured on a substrate, measuring an intensity of the light that is reflected off of at least one of the film and the substrate and determining a level of cure of the film based at least in part on the intensity of the light. The light is emitted toward the film and substrate at an angle between 0° and 20° with respect to an axis normal to the film and the substrate.

A measurement system includes an infrared light source that emits infrared light, a substrate that includes a light-activated resin film, an optical filter that is positioned to receive the infrared light that is reflected off of the substrate and/or the film, and an optical detector that is positioned to detect the infrared light that is received by the optical filter. The infrared light is emitted onto the substrate at an angle with respect to an axis that is normal to the substrate. The film and the substrate reflect at least a portion of the infrared light that is emitted by the infrared light source.

DETAILED DESCRIPTION

With the growing popularity of light-curing devices involved in curing processes, specifically ink curing processes, the ability to monitor whether the cure is complete or at what level of cure the light-activated resin is without disrupting the curing process has become a very useful and almost critical tool. The current technologies used to monitor the curing process are either very expensive, such as the FTIR spectrophotometer, or are rudimentary and subjective, such as the tape and rub tests. None of the currently available monitoring options has the ability to provide low-cost, accurate, real-time monitoring capabilities without disrupting the curing process.

Figure 1:
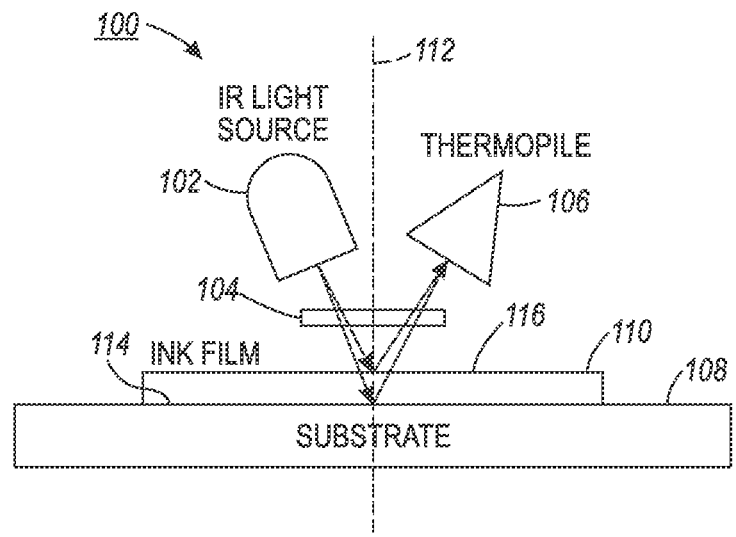
FIG. 1 shows a monitoring device in accordance with some aspects of the disclosure.

FIG. 1 shows an example monitoring device 100 that includes a light source 102, an optical filter 104, and an optical detector 106 that provides low-cost, accurate, real-time monitoring of the curing processes. The light source emits light toward a substrate 108 to which a film 110 is attached or cured. The light reflected off of the substrate 108 and off of the ink film 110 is received through the optical filter 104 and is detected by the optical detector 106. The optical filter 104 can be coaxial with the optical detector 106 to prevent extra reflections in the system.

The monitoring device 100 shown in FIG. 1 may be included in any suitable environment including being embodied in a sensor attached to or otherwise electrically coupled to a light-curing device that emits the light that causes the curing of the film to occur. The monitoring device 100 helps to monitor the level of cure of any light-activated material, including light-activated resins, and can be positioned anywhere with respect to the material being cured so that the monitoring device 100 can effectively monitor the level of cure of the light-activated material(s). For example, the light activated material(s) can include ultraviolet (UV) light-activated photo-polymerizable and cross-linkable materials. The monitoring device 100 itself does not cause the light-activated material to cure, but may be included in a larger system or device that does control the curing of the light-activated material in some examples. In other examples, the monitoring device may be a separate element from the light-curing device or system.

The light source 102 of the monitoring device 100 shown in FIG. 1 is any suitable light source that emits continuous or modulated light toward the film 110 and substrate 108 combination such that the light reflected off of the film 110 and substrate 108 indicates a level of cure of the film 110 or other light-activated material on the substrate 108. To determine the level of cure of the film 110, the level of relative concentration of monomers and oligomers in the film 110 may be measured. The level of cure is directly related to the concentration of the polymerization of the monomers and oligomers in the film 110. As this polymerization occurs, the number of vibrational absorptions modes of the film 110 decreases, which leads to an increase in transmission of light in the infrared region. In some examples, the range within which the reduction in absorption is best seen is light having a wavelength between 6 μm and 12 μm.

Figure 2:
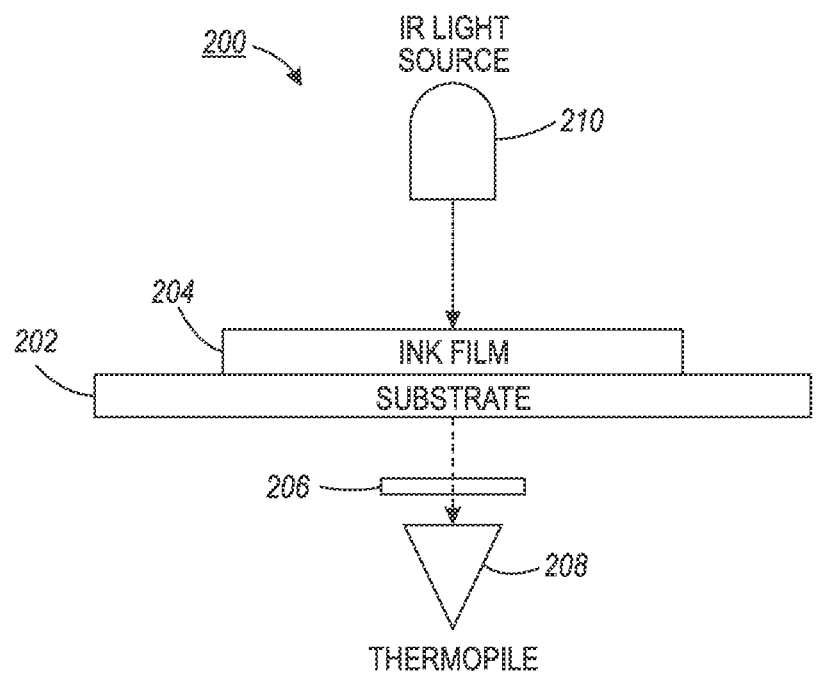
FIG. 2 shows another embodiment of a monitoring device in accordance with aspects of the disclosure.

By measuring the intensity of the light reflected off of the film and/or substrate, the relative concentration of free monomers and oligomers remaining in the film can be measured. Depending on the type of substrate, as the curing process progresses, the amount of light either reflected off of or transmitted through the film and substrate increases. FIG. 1 shows a monitoring device 100 in which the substrate 108 is absorptive and thus the light emitted toward the film 110 and substrate 108 is either reflected off of one or both of the film 110 and substrate 108 or is absorbed by the substrate 108. FIG. 2 shows another embodiment of a monitoring device 200 in which the substrate 202 is emissive and thus light is either absorbed by the film 204 and/or substrate 202 or is transmitted through the substrate 202.

The substrate is any suitable substrate, including quartz, paper, plastic, and the like. The substrate is typically considered either emissive, reflective, or transmissive. Emissive substrates absorb light. As discussed above, the monitoring device 100 shown in FIG. 1 emits light toward a reflective substrate 108 and the monitoring device 200 shown in FIG. 2 emits light toward a translucent substrate 202.

The light-activated material undergoing the curing process is any suitable light-activated material that may be used to cure ink in printing processes, cure coatings on various materials such as wood, metals, and plastics, cure adhesives used to adhere two elements together, and the like. The light-activated material may be a light-activated resin that cures and quickly hardens when exposed to certain wavelengths of light, such as ultraviolet light. In another example, the light-activated material is an ink or a film that is applied to a substrate, such as paper or plastic. When light, such as ultraviolet light, is emitted toward the substrate with such a light-activated ink or film, the ink or film becomes "cured" or otherwise hardened or dried.

As discussed above, the monitoring device includes an optical filter and an optical detector. The optical filter is positioned so that a wavelength of the light is transmitted through the optical filter after the light is reflected off of or transmitted through the substrate and/or the film. The optical filter may receive a particular wavelength or range of wavelengths of light that is reflected off of or transmitted through the substrate and/or the film in some examples. For example, the optical filter includes a bandpass filter that only permits a predetermined range of wavelengths of light to be transmitted through the optical filter and toward the optical detector. In some examples, the range of wavelengths may be 6-12 μm. In other examples, the optical filter may receive all wavelengths of light that are reflected off of the substrate and/or film.

The optical filter directs the reflected light toward the optical detector. The optical detector is any suitable detector that is capable of detecting the intensity of the light that is transmitted through the optical filter. In some examples, the optical detector includes a low-cost infrared detector when the light reflected off of the substrate and/or film includes light having a wavelength in the infrared range. For example, the optical detector is a thermopile that converts thermal energy into electrical energy by detecting an intensity of light and translating that intensity of light into a respective voltage output.

Referring again to FIG. 1, the monitoring device 100 has an infrared (IR) light source 102, an optical filter 104, and an optical detector 106. As shown in FIG. 1, the IR light source 102 emits light toward a film 110 that is attached or cured to a substrate 108. In this example, the film 110 is an ink and the substrate 108 is paper. While reference is made to the ink or more generally the film being "attached" to the paper or more generally the substrate, the term "attached" refers to the ink being placed on the paper prior to and throughout the curing process. As curing progresses, the ink becomes hardened and dried and thus becomes "cured" to the paper. However, the term "attached" is meant to include any positioning of the ink and the paper together throughout the curing process.

As shown in FIG. 1, the IR light source 102 emits light toward the ink 110 and substrate 108 at an angle. The angle at which the IR light source 102 emits light may vary. For example, the IR light source 102 emits light toward the substrate 108 and ink 110 at an angle of approximately 10° with respect to an axis 112 normal to the substrate 108 and the ink 110. The angle may be greater than or less than 10°, but may not be exactly or approximately 90° with respect to the axis 112 normal to the substrate 108 and film 110. When the IR light source 102 (or any other light source) emits light toward the substrate 108 and film 110 at a 90° angle, the light is directly reflected back toward the IR light source 102 at the complementary 90° angle and the light cannot be easily measured. For example, the angle at which the light is emitted toward the film 110 and the substrate 108 may be between 0° and 45° in some examples and between 0° and 20° in other examples with respect to the axis 112 that is normal to the film 110 and the substrate 108.

As shown by the arrows in FIG. 1, the light emitted from the IR light source 102 is emitted toward the ink film 110 and the substrate 108. A portion of the light is transmitted through the ink film 110 and contacts the substrate 108. Some of the light contacting the substrate 108 is absorbed into the substrate 108. However, the majority of the light that contacts the substrate 108 in FIG. 1 is reflected off of the substrate and is again transmitted through the ink film 110, as indicated by the arrows. Because some of the light is reflected off of the ink film 110 and some of the light is reflected off of the substrate 108, an ink film-substrate boundary 114 and an air-ink film boundary 116 are created at which the light is reflected. The increasing intensity of the reflected light is a result of the ink film 110 becoming more transparent as the curing process progresses, which permits more light to be transmitted through the ink film 110 to the substrate 108 and then reflected off of the substrate 108 at the ink film-substrate boundary 114. As the curing process progresses the portion of the emitted light that is reflected off of the ink film 110 decreases and the portion of the emitted light that is reflected off of the substrate 108 increases.

The angle at which the light is reflected off of the ink film 110 and the substrate 108 depends on the angle at which it is emitted toward the ink film 110 and the substrate 108. For example, the IR light source 102 in FIG. 1 emits light toward the ink film 110 and the substrate 108 at an angle of approximately 10° and the light that is reflected off of the ink film 110 at the air-ink film boundary 116 and the light that is reflected off of the substrate 108 at the ink film-substrate boundary 114 is reflected off of the respective boundaries at an angle of 10° as well. The angle of reflection will correspond to the angle at which the light is emitted toward the ink film 110 and substrate 108.

The optical filter 104 of the monitoring device 100 shown in FIG. 1 is positioned so that the light that is reflected off of the ink film 110 and the substrate 108 is received through the optical filter 104. In this example configuration, the light source 102, the optical filter 104, and the optical detector 106 are positioned on the same side of the ink film 110 and substrate 108 (cf. FIG. 2 in which the light source is on the opposite side of the ink film and substrate from the optical filter and the optical detector, which is discussed below). The optical filter receives the light reflected off of the ink film and substrate and the optical detector is able to detect the light transmitted through the optical detector. In this example, the optical detector includes a thermopile that translates the detected intensity of the light into a corresponding voltage.

FIG. 2 shows an alternative embodiment of the monitoring device 200 in which the substrate 202 is a transmissive substrate, such as quartz. The function of the monitoring device 200 shown in FIG. 2 is similar in nature to the monitoring device 100 shown in FIG. 1, with the exception that the optical filter 206 and the optical detector 208 are positioned on opposite sides of the ink film 204 and substrate 202 from the IR light source 210. However, the monitoring device 200 shown in FIG. 2 measures the intensity of the light in the same manner as the monitoring device 200 shown in FIG. 1. For example, the IR light source 210 of FIG. 2 emits light toward the ink film 204 and the substrate 202. A portion of the light is absorbed by the ink film 204 and a portion of the light is transmitted through the ink film 204 and through the substrate 202. In this example, the substrate 202 is considered emissive, which means that light will pass through the substrate 202 and continue its path on the opposite side of the substrate 202 from the IR light source 210, as indicated by the arrows in FIG. 2. The optical filter 206 and the optical detector 208 are positioned on the opposite side of the substrate 202 from the IR light source 210 in the monitoring device 200 shown in FIG. 2. As the curing process progresses, the ink film 204 becomes increasingly transparent, which allows for an increasing intensity of light to be transmitted through to the substrate 202 and thus the opposite side of the substrate 202 from the IR light source 210 so that it can be received by the optical filter 206 and detected by the optical detector 208.

Figure 3:
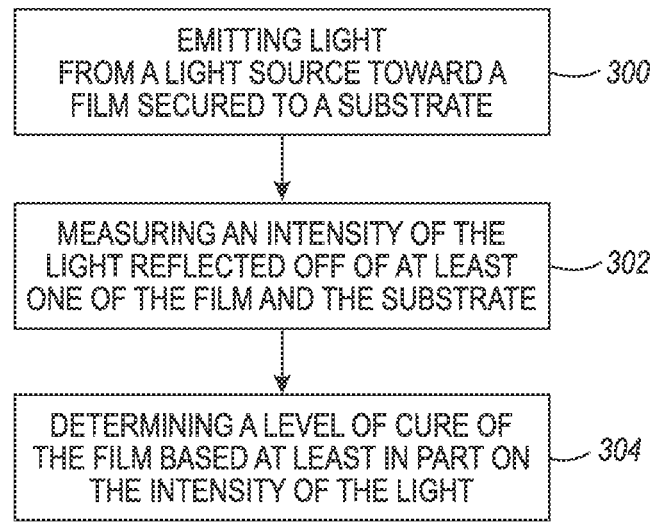
FIG. 3 shows a method of monitoring a level of cure of a film attached to a substrate.

FIG. 3 shows various steps in a method of monitoring the curing level of a light-activated material. For example, light is emitted from a light source toward a light-activated material, such as an ink or other type of film, which is attached to a substrate 300. Then, the intensity of the light that is reflected off of one or both of the film and the substrate is measured 302. A level of cure of the film is determined based at least in part on the intensity of the measured light 304. Other steps may be optionally included in this process.

Figure 4:
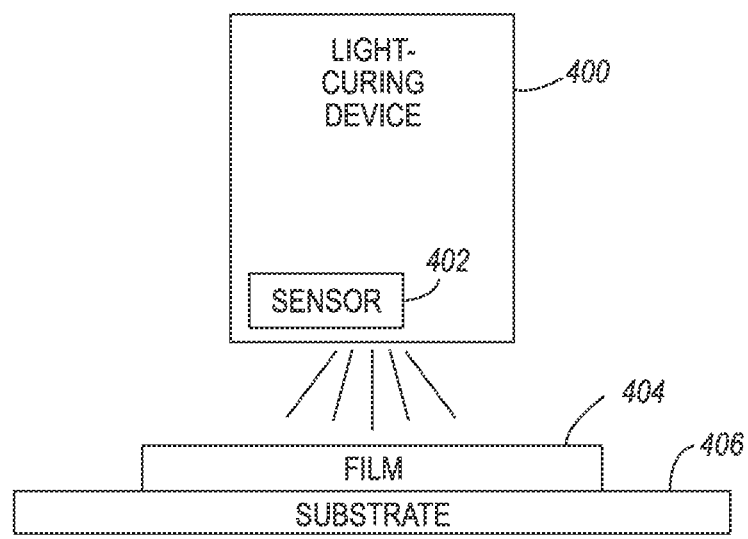
FIG. 4 shows an example of a monitoring device embodied in a sensor and attached to a light-curing device.

FIG. 4 shows a system in which a light-curing device 400 includes a sensor 402 attached to it. The light-curing device 400 emits light, in some examples ultraviolet light, toward the film 404 and substrate 406. In this example, the sensor 402 includes a monitoring device that monitors the level of cure of the film as the curing process progresses. The monitoring device is any of the examples described above and includes an IR light source that also emits light toward the film and substrate to determine the level of cure based on the intensity of the light that is reflected off of the film 404 and the substrate 406. In some examples, the sensor 402 can be approximately 2 mm×4 mm, although it can be any suitable size and shape.

It will be appreciated that variations of the above-disclosed monitoring devices and methods and other features and functions, or alternatives thereof, may be desirably combined into many other different systems, methods, or applications. For example, monitoring curing processes may use any one or more of the above monitoring devices. Also various presently unforeseen or unanticipated alternatives, modifications, variations, or improvements therein may be subsequently made by those skilled in the art which also are intended to be encompassed by the following claims.

The invention claimed is:

1. A sensor, comprising:
    a light source that is configured to emit infrared light towards an ultraviolet light-activated film during a curing process to cure the ultraviolet-activated film to a substrate, the ultraviolet light-activated film forming a continuous layer on the substrate;
    an optical filter positioned so that a wavelength of the light is transmitted through the optical filter after the infrared light is reflected off of the substrate at an ultraviolet light activated film-substrate boundary and the ultraviolet light-activated film at an air-ultraviolet light activated film boundary during the curing process; and
    an optical detector positioned to detect the infrared light reflected off of the ultraviolet light activated film-substrate boundary and the air-ultraviolet light-activated film boundary that is transmitted through the optical filter;
    wherein the sensor is configured to determine a level of cure of the ultraviolet light-activated film to the substrate, the level of cure determined in real-time during the curing process, the level of cure based on the detected infrared light reflected off of the ultraviolet light activated film-substrate boundary and the air-ultraviolet light activated film boundary.

2. The sensor of claim 1, wherein the optical filter is a bandpass optical filter.

3. The sensor of claim 1, wherein the wavelength of the reflected infrared light at the ultraviolet light activated film-substrate boundary and at the air-ultraviolet light activated film boundary is within a range of 6 micrometers to 12 micrometers.

4. The sensor of claim 1, wherein the substrate includes at least one of paper and plastic.

5. The sensor of claim 1, wherein the ultraviolet light-activated film includes an ultraviolet light-activated resin.

6. The sensor of claim 5, wherein the ultraviolet light-activated resin includes an ultraviolet light activated photopolymerizable and cross-linkable material.

7. The sensor of claim 1, wherein the ultraviolet light-activated film is an ultraviolet light-activated ink film.

8. The monitoring device of claim 1, wherein the combination of the ultraviolet light-activated film layered on the substrate includes a first surface and an opposing second surface, and wherein the light source, the optical filter, and the optical detector are positioned spaced apart from the first surface.

9. The sensor of claim 1, wherein the combination of the ultraviolet light-activated film layered on the substrate includes a first surface and an opposing second surface, and wherein the light source is positioned spaced apart from the first surface and the optical filter and the optical detector are positioned spaced apart from the second surface.

10. The sensor of claim 1, wherein the light source emits light at an angle between 0° and 45° with respect to an axis normal to the substrate and the ultraviolet light-activated film.

11. The sensor of claim 10, wherein the light source emits light at an angle of 10° with respect to an axis normal to the substrate and the ultraviolet light-activated film.

12. The sensor of claim 10, wherein the optical filter and the optical detector are positioned at an angle between 0° and 45° with respect to an axis normal to the substrate and the ultraviolet light-activated film.

13. The sensor of claim 12, wherein the optical filter and the optical detector are positioned at an angle of 10° with respect to the axis normal to the substrate and the ultraviolet light-activated film.

14. The sensor of claim 1, wherein the optical detector includes a thermopile configured to translate the detected infrared light from the ultraviolet light activated film-substrate boundary and the air-ultraviolet light activated film boundary into respective voltage values.

15. The sensor of claim 14, wherein the respective voltage values correspond with relative concentrations of monomers and oligomers in the ultraviolet light-activated film and the level of cure directly relates to the concentration of polymerization of the monomers and the oligomers in the ultraviolet light-activated film, the concentration of polymerization of the monomers and the oligomers indicative of a transmission of light in an infrared wavelength region.

16. A method, comprising:

emitting infrared light from a light source toward an ultraviolet light-activated film layered on a substrate at an angle between 0° and 20° with respect to an axis normal to the ultraviolet light-activated film and the substrate, the infrared light emitted during a curing process of curing the ultraviolet light-activated film to the substrate;

detecting, during the curing process, reflected infrared light reflected off of the substrate at an ultraviolet light-activated film-substrate boundary and the ultraviolet light-activated film at the air-ultraviolet light-activated film boundary;

measuring, in real-time during the curing process, the intensity of the light reflected off of the substrate at the ultraviolet light-activated film-substrate boundary and the light reflected off of the ultraviolet light-activated film at the air-ultraviolet light-activated film boundary; and determining, in real-time during the curing process, a level of cure of the ultraviolet light-activated film based at least in part on the measured intensity of the light reflected off of the substrate at the ultraviolet light-activated film-substrate boundary and the light reflected off of the ultraviolet light-activated film at the air-ultraviolet light-activated film boundary.

17. The method of claim 16, wherein the step of measuring the intensity of the reflected light from the ultraviolet light-activated film-substrate boundary and the reflected flight from the air-ultraviolet light-activated film boundary includes receiving the light through an optical filter and detecting the light with an optical detector after the light is received through the optical filter.

18. The method of claim 16, wherein the ultraviolet light-activated film includes an ultraviolet light-activated resin.

19. The method of claim 16, wherein the light source is positioned on a first side of the ultraviolet light-activated film layered on the substrate and the reflected light is detected from the first side.

20. The method of claim 16, wherein the determining the level of cure of the ultraviolet light-activated film based at least in part on the measured intensity of the reflected light includes measuring the relative concentration of monomers and oligomers in the ultraviolet light-activated film during the curing process.

21. A sensor, comprising:

an infrared light source that is configured to emit infrared light towards an ultraviolet light-activated resin film during a curing process to cure the ultraviolet-activated film to a substrate, the ultraviolet light-activated film forming a continuous layer on the substrate, the ultraviolet light-activated resin positioned to receive the infrared light at an angle with respect to an axis that is normal to the substrate and that reflects infrared light off of the substrate at an ultraviolet light-activated resin film-substrate boundary and off of the ultraviolet light-activated resin film at an air-ultraviolet light-activated resin film boundary;

an optical filter positioned to receive the infrared light reflected off of the substrate at the ultraviolet light-activated resin film-substrate boundary and off of the ultraviolet light-activated resin film at the air-ultraviolet light-activated resin film boundary; and an optical detector positioned such that the infrared light reflected off of the substrate and off of the ultraviolet light-activated resin film is received by the optical filter and is detected by the optical detector;

wherein the sensor is configured to determine a level of cure of the ultraviolet light-activated resin film based on the detected infrared light reflected off of the substrate and off of the ultraviolet light-activated resin film.

22. The monitoring system of claim 21, wherein the optical detector includes a thermopile configured to translate the detected infrared light reflected off of the substrate and off of the ultraviolet light-activated film into respective voltage values correspond with relative concentration of monomers and oligomers in the ultraviolet light-activated film.

* * * * *